US00PP18672P2

(12) United States Plant Patent
Olsthoorn

(10) Patent No.: US PP18,672 P2
(45) Date of Patent: Apr. 1, 2008

(54) *SPATHIPHYLLUM* PLANT NAMED '96411-10'

(50) Latin Name: *Spathiphyllum Schott*
Varietal Denomination: 96411-10

(75) Inventor: Petrus C. M. Olsthoorn, Honselersdijk (NL)

(73) Assignee: P.C.M. Olsthoorn Holding BV, Honselersdijk (NL)

( * ) Notice: Subject to any disclaimer, the term of this patent is extended or adjusted under 35 U.S.C. 154(b) by 0 days.

(21) Appl. No.: 11/581,177

(22) Filed: Oct. 13, 2006

(51) Int. Cl.
*A01H 5/00* (2006.01)

(52) U.S. Cl. ..... Plt./364

(58) Field of Classification Search ..... Plt./364
See application file for complete search history.

*Primary Examiner*—Kent Bell
*Assistant Examiner*—Annette H Para

(57) ABSTRACT

A new cultivar of *Spathiphyllum* plant named '96411-10' that is characterized by white spathes, green leaves, early branching and a good response to plant growth regulators.

1 Drawing Sheet

Botanical Classification: *Spathiphyllum Schott. Variety Denomination:* '96411-10'.

BACKGROUND OF THE INVENTION

The present invention relates to a new and distinct cultivar of *Spathiphyllum* plant botanically known as *Spathiphyllum Schott.* and hereinafter referred to by the cultivar name '96411-10'.

'96411-10' is a hybrid that originated from the hybridization of the female or seed parent a proprietary *Spathiphyllum Schott.* identified as '94162-1' (not patented) and the male or pollen parent a proprietary *Spathiphyllum Schott.* identified as '95280-46' (not patented). The cultivar '96411-10' was selected by the inventor in February of 1998 as a single plant within the progeny of the stated cross in Honselersdijk, The Netherlands.

Asexual reproduction by tissue culture of the new cultivar '96411-10' was first performed in February of 1999 in Honselersdijk, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Spathiphyllum* cultivar '96411-10'.

1. *Spathiphyllum* '96411-10' exhibits white spathes.
2. *Spathiphyllum* '96411-10' exhibits green leaves.
3. *Spathiphyllum* '96411-10' exhibits early branching.
4. *Spathiphyllum* '96411-10' responds well to plant growth regulators.

The closest comparison cultivar is *Spathiphyllum* 'Sweet Pablo' (U.S. Plant Pat. No. 10,817). The new cultivar '96411-10' is distinguishable from 'Sweet Pablo' by the following characteristics:

1. '96411-10' has wavy leaf margins. 'Sweet Pablo' does not have wavy leaf margins.
2. '96411-10' has more spathes than 'Sweet Pablo'.

The new cultivar '96411-10' is distinguishable from the male parent *Spathiphyllum* '95280-46' in having more spathes and a better response to plant growth regulators. The new cultivar '96411-10' is distinguishable from the female parent. *Spathiphyllum* '94162-1' in having more spathes and a better response to plant growth regulators.

BRIEF DESCRIPTION OF THE DRAWING

The accompanying photograph illustrates the distinguishing traits of *Spathiphyllum* '96411-10'. The plant in the photograph shows an overall view of a 29 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Spathiphyllum* cultivar named '96411-10'. Data was collected in Honselersdijk, The Netherlands from 29 week old greenhouse grown plants in 2 liter containers. The time of year was Spring and the average temperature was 22 degrees Centigrade during the day and 20 degrees Centigrade at night. No photoperiodic treatments were used. 60 PPM of Gibberallic acid was applied for flower initiation. Color determinations are in accordance with The Royal Horticultural Society Colour Chart 2001 edition, except where general color terms of ordinary dictionary significance are used. The growing requirements are similar to the species. '96411-10' has not been tested under all possible conditions and phenotypic differences may be observed with variations in environmental, climatic, and cultural conditions, however, without any variance in genotype.

Botanical classification: *Spathiphyllum Schott.* '96411-10'.
Use: Ornamental.
Parentage: '96411-10' is a hybrid plant that resulted from the hybridization of the following parent plants:
- *Female parent.*—A proprietary *Spathiphyllum Schott.* identified as '94162-1'.
- *Male parent.*—A proprietary *Spathiphyllum Schott.* identified as '95280-46'.

Vigor: Moderate.

Growth rate: Moderate.
Growth habit: Freely branching from base, bushy and dense.
Plant shape: Inverted triangle with inflorescences on top.
Suitable container size: 17 cm container.
Height: Average 55 cm to top of leaf plane, 67 cm to top of inflorescences.
Width: Average 63.5 cm in width.
Hardiness: USDA Zone 10.
Propagation: Tissue Culture.
Time to initiate roots (summer and winter): Approximately 14 days to produce roots on an initial cutting.
Time to produce a rooted cutting or liner (summer and winter): Approximately 38 days.
Root system: Fine and fibrous.
Stem: No stems, Leaves grow directly from base, Average 3 clumps, clump color 144A to 144B.
Foliage:
*Texture.*—Smooth, slightly leathery.
*Appearance.*—Glossy.
*Leaf arrangement.*—Alternate.
*Compound of or single.*—single.
*Leaf shape.*—Elliptic to narrow elliptic.
*Leaf apex.*—Apiculate.
*Leaf base.*—Attenuate.
*Leaf length.*—Average 29.6 cm in length.
*Leaf width.*—10.3 cm in width.
*Quantity of leaves per clump.*—Average 5.
*Pubescence.*—Absent.
*Leaf margin.*—Entire, undulant; 10 waves per leaf.
*Vein pattern.*—Pinnate.
*Young leaf color* (*upper surface*).—143A.
*Young leaf color* (*lower surface*).—137B to 137B.
*Mature leaf color* (*upper surface*).—137A 139A.
*Mature leaf color* (*lower surface*).—137B to 137C.
*Vein color* (*upper surface*).—141A.
*Vein color* (*lower surface*).—144B.
*Leaf attachment.*—Petiolate.
*Petiole dimensions.*—Average 24 cm in length excluding geniculum, 4 mm in diameter below geniculum to 5 mm in diameter above clump.
*Petiole aspect.*—Round.
*Petiole color.*—137A, lighter towards the base 143C.
*Geniculum dimensions.*—Average 2.2 cm in length and 4.5 mm in diameter.
*Geniculum aspect.*—Rounded, glossy, glabrous.
*Geniculum color.*—144B.
*Petiole sheath dimensions.*—Average 17.7 cm in length and 5 mm in diameter.
*Petiole sheath color.*—137A lighter towards the base, 143A.
*Durability of foliage to stress.*—High.
Inflorescence:
*Inflorescence arrangement.*—Spathes with spadices held above the foliage on erect peduncles arising from the petiole sheath.
*Flowering habit.*—Continuous.
*Quantity of spathes per plant.*—Average 11.
*Natural flowering season.*—Autumn to winter to spring.
*Time to flower or response time.*—6 months.
*Fragrance.*—Moderate, acid-sweet; pleasant.
*Self*-cleaning or persistent.—Persistent.
*Flower longevity.*—Lasts approximately 3 weeks on plant.
*Spathe aspect.*—Slightly cupped.
*Spathe dimensions.*—Average 14.8 cm in length, 6.1 cm in width and 4.1 cm in depth.
*Spathe texture.*—Glabrous, slightly leathery.
*Spathe shape.*—Elliptic to broad elliptic.
*Spathe margin.*—Entire.
*Spathe apex.*—Apiculate.
*Spathe base.*—Cuneate.
*Spathe color when opening* (*front side*).—N155A, apex 138C.
*Spathe color when opening* (*rear side*).—N155A, apex and base 144A; main vein N144A.
*Spathe color when fully opened* (*front side*).—N155A, apex 138C.
*Spathe color when fully opened* (*rear side*).—N155A, apex and base 144A; main vein N144A.
*Spathe color fading to.*—143A to 143C.
*Spadix shape.*—Columnar, arising from top of peduncle.
*Spadix tip.*—Obtuse.
*Spadix base.*—Obtuse.
*Spadix dimensions.*—Average 5.9 cm in length and 1.5 mm in diameter.
*Spadix color when opening.*—4D.
*Spadix color when fully opened.*—158D.
*Quantity of flowers per spadix.*—Average 160.
*Spadix flower arrangement.*—Bisexual, rounded.
*Spadix flower dimensions.*—3.5 mm in diameter and 3 mm in depth.
Reproductive organs.
*Anther color.*—158B to 158C.
*Amount of pollen.*—High.
*Pollen color.*—155D.
*Stigma color.*—158A.
*Ovary color.*—158B to 158C.
Peduncle:
*Peduncle dimensions.*—Average 43.7 cm in length and 4.0 mm. in diameter.
*Peduncle angle.*—10° from vertical.
*Peduncle color.*—143A.
*Peduncle strength.*—Strong.
Seed: Seed production has not been observed.
Disease and insect resistance: Plants of the new *Spathiphyllum* have not been observed for disease or insect resistance.

It is claimed:

1. A new and distinct variety of *Spathiphyllum* plant named '96411-10' as described and illustrated.

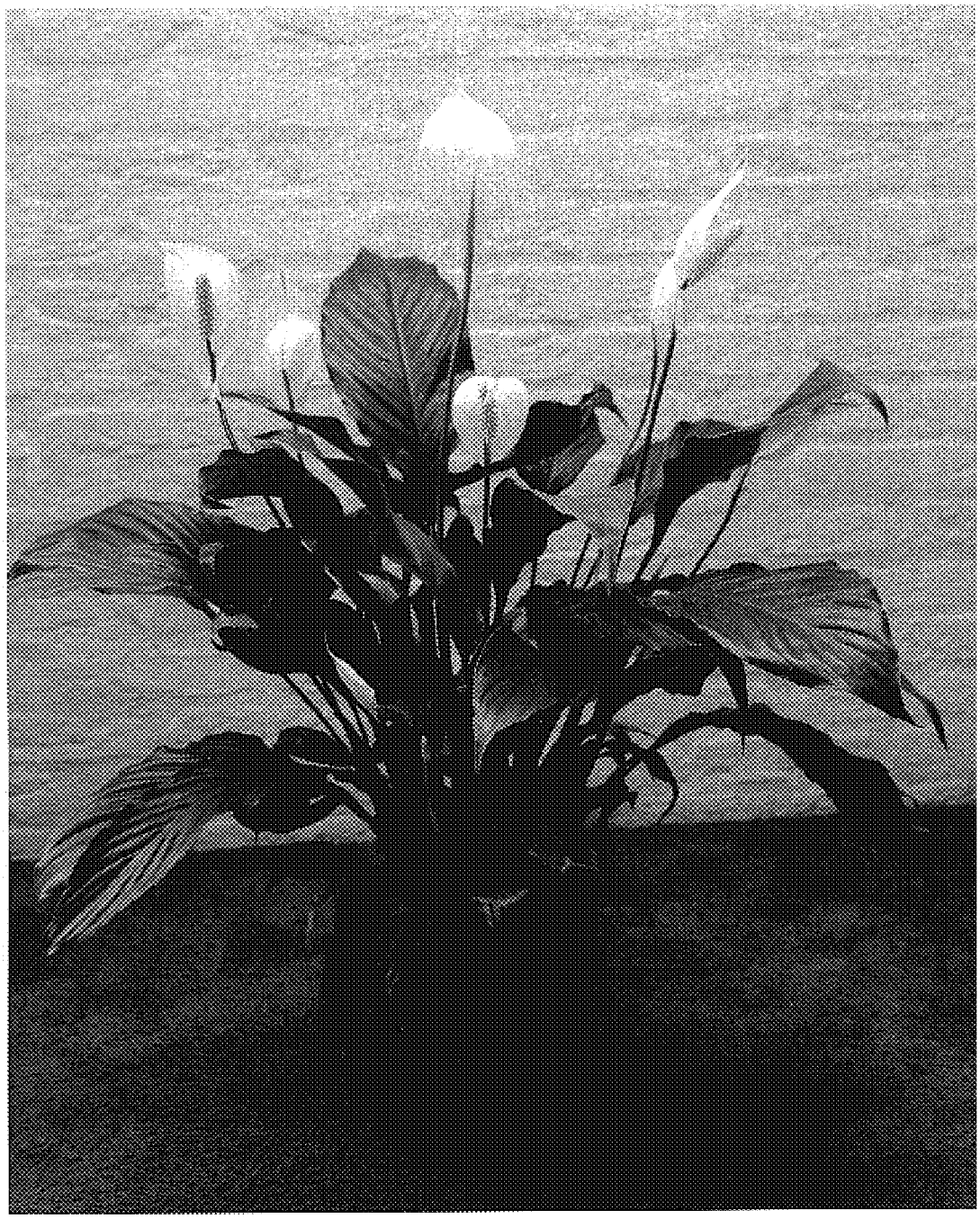

* * * * *